United States Patent [19]

Matthiessen et al.

[11] Patent Number: 4,707,614
[45] Date of Patent: Nov. 17, 1987

[54] SELF-CONTAINED PORTABLE PHOTOELECTRIC GAS MEASURING AND WARNING APPARATUS

[75] Inventors: Hans Matthiessen, Gross Parin; Jörg Winkler, Stockelsdorf, both of Fed. Rep. of Germany

[73] Assignee: Drägerwerk Aktiengesellschaft, Lübeck, Fed. Rep. of Germany

[21] Appl. No.: 819,140

[22] Filed: Jan. 15, 1986

[30] Foreign Application Priority Data

Jan. 15, 1985 [DE] Fed. Rep. of Germany ....... 3501093

[51] Int. Cl.4 ............................................. G01N 21/49
[52] U.S. Cl. ..................................... 250/576; 356/442
[58] Field of Search ................ 250/577, 576; 356/442; 422/81, 39; 73/293

[56] References Cited

U.S. PATENT DOCUMENTS 3,773,424 11/1973 Selgin ................................. 250/576
4,084,426 4/1978 Gales ................................. 250/577
4,123,227 10/1978 Heim et al. .......................... 250/577
4,450,722 5/1984 Keyes IV et al. .................. 250/577
4,558,947 12/1985 Wardlaw ............................. 356/39

Primary Examiner—Edward P. Westin
Assistant Examiner—Jessica L. Ruoff
Attorney, Agent, or Firm—Walter Ottesen

[57] ABSTRACT

A gas measuring and warning apparatus is disclosed having a testing tube through which the gas that is to be detected flows. The apparatus also has a photoelectric scanner for detecting the migrating reaction zone. The configuration of the apparatus is simplified and the resolution capacity is improved. This is achieved in that the photoelectric scanner includes an image forming lens system which forms an image of the length of the reaction zone on a photosensitive array of identical sensor elements, the reaction zone being illuminated by at least one light source. For emitting a measured signal, the evaluation circuit is controlled by the number of sensor elements that are located within the imaged length of the reaction zone.

8 Claims, 3 Drawing Figures

SELF-CONTAINED PORTABLE PHOTOELECTRIC GAS MEASURING AND WARNING APPARATUS

FIELD OF THE INVENTION

The invention relates to a gas measuring and warning apparatus with a testing tube through which the gas that is to be detected flows. A photoelectric scanner scans the testing tube at a number of locations spaced apart from one another along the direction of flow, so that by means of an evaluation circuit connected to the photoelectric scanner, a reaction zone that migrates through the testing tube can be detected.

BACKGROUND OF THE INVENTION

Testing tubes filled with a chemical reagent are used to determine gaseous components in gas mixtures that are aspirated or pressed through the testing tube. The reaction taking place with the powdered or granulated reagent produces a reaction zone marked by a change in color. The length of this zone is proportional to the quantity of the gas component which has flowed into the testing tube and to which the reagent specifically responds. If the quantity of the gas mixture passing through the testing tube is known, then the proportion of the gas component to be detected, or its concentration, can be ascertained from the length of the reaction zone.

German Pat. No. 2,840,867 discloses a gas measuring device wherein the migration of the reaction zone in the testing tube is ascertained by means of a photoelectric scanner and is specified as a measured quantity via a receiver connected thereto. The testing tube is uniformly illuminated by a light source, and the light radiation reflected by the reaction zone is determined in a receiver via fiber optics with light conductors. This kind of measuring device affords monitoring of the advancing length of the reaction zone without having any moving parts, and it enables electrical measurement or control signals to be derived which not only indicate the concentration of the component that is to be detected, but also trigger an alarm device in the event that predetermined limit values are exceeded

SUMMARY OF THE INVENTION

It is an object of the invention to provide a gas measuring and warning apparatus of the above-described type, such that without moving parts and using simple circuit means, a multiplicity of measured length values can be ascertained and processed in a desired manner. A further object is to attain sharp and unequivocal distinction, with high resolution, at the boundary of the reaction zone.

The above objects are realized with the apparatus according to the invention. The apparatus includes a photoelectric scanner having an image forming lens system for imaging the length of the reaction zone, which is illuminated by at least one light source, on a photosensitive array of identical sensor elements. For providing a measurement signal, the evaluation circuit is controlled by those sensor elements that are located within the imaged length of the reaction zone.

Such an apparatus can be equipped with various sensors, but preferably with a photosensitive diode array. Instead of the heterogeneous sensor array, a homogeneous sensor array can be suitably used if desired; in that case, instead of the many individual measured values of the heterogeneous sensor array, a single analog measured value, such as a resistance value, is obtained.

A particular advantage can possibly be obtained by causing the imaging lens system to furnish an enlarged image, so that the image of the length of the reaction zone is distributed over a greater number of sensor elements. In this way, the resolution can be increased.

It also appears suitable for the light source that is used to be disposed with respect to the testing tube such that the array of sensors is located outside the glancing angle of the testing tube, which has a reflective surface. Distortion of the desired image of the reaction zone is thereby avoided. Additional filter elements, which increase the contrast between the imaged reaction zone and the remaining portion of the length of the testing tube, can be disposed between the light source and the testing tube as required.

To compensate for a drift error, it appears advantageous to provide a special reference remission surface at the end of the evaluatable reaction zone of the testing tube, and to derive a signal for drift correction from the image of this reference remission surface at the end of the sensor array. This makes it possible to exclude the effects of temperature and other factors.

If a diode array is used, the evaluation circuit suitably includes a preamplifier, an analog and digital converter, a first digital memory for the scanned values prior to feeding in gas, a second digital memory for the scanned values after gas has been fed in, and a digital arithmetic unit connected to an indicator or alarm device.

In an advantageous embodiment, a holder for the testing tube, which can be connected to a flow inducer, is located in the upper part of the housing, and two lamps are disposed in the lower part of the housing so as to be symmetrical with respect to a deflection mirror for deflecting the beam path from the illuminated testing tube into the image forming lens system which may comprise only a single focusing lens as required. The diode array is disposed behind the image forming lens system and has terminals connected to the evaluation circuit.

The measuring apparatus of the invention reliably monitors the reaction zone with high resolution. In addition, the measuring apparatus is in a compact, space-saving configuration and can even be accommodated in a portable unit.

BRIEF DESCRIPTION OF THE DRAWING

The invention will now be described with reference to the drawing wherein.

DESCRIPTION OF THE PREFERRED EMBODIMENTS OF THE INVENTION

Figure 1:
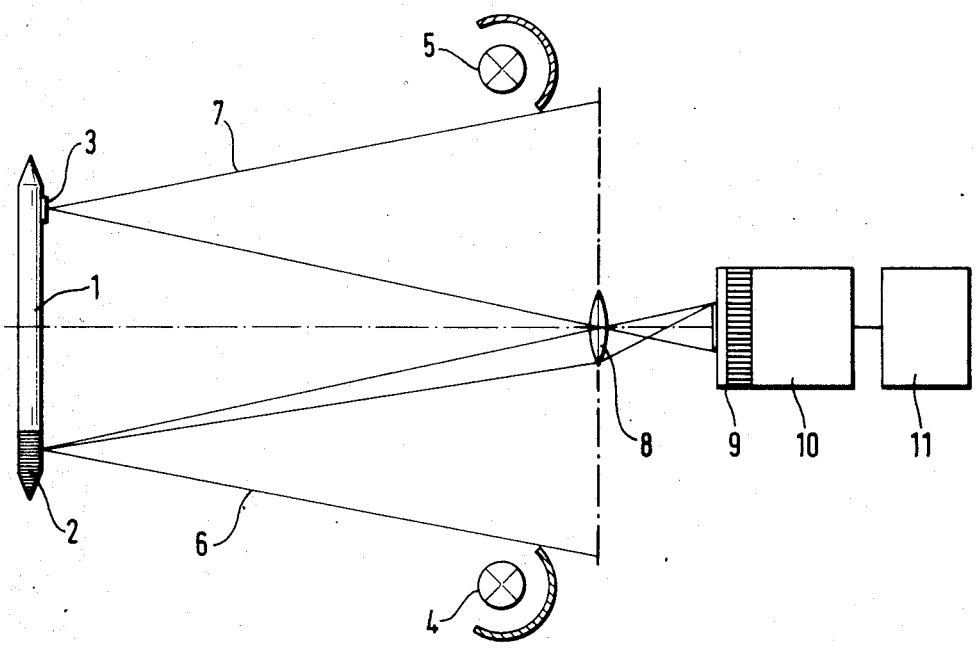
FIG. 1 explains the principle of the optical image formation of the testing tube.

In FIG. 1, a testing tube 1 is shown in which a reaction zone 2 has formed. A reference-remission surface 3 is located at the end of the usable length of the testing tube 1. The testing tube 1 is uniformly illuminated by two lamps 4 and 5. Along the lines 6 and 7, there is an inner limitation of the illumination to prevent reflections on the glass surface of the testing tube.

The testing tube 1 is imaged onto a diode line or diode array 9 by an image forming lens system 8 which is configured as a focusing lens. The number of diodes in an actual embodiment may be from several hundred to a thousand.

The output signals of the diode array 9 are fed into an evaluation circuit 10, which makes it possible to read out the diode array at a suitably predetermined clock rate via a built-in shift register. The evaluation circuit 10 includes a preamplifier, as well as an analog-to-digital converter, which converts the signals read out from the diode array into digital signals, as well as a first digital memory in which these signals, picked up prior to feeding gas into the testing tube, are stored. The evaluation circuit also includes a second digital memory, which stores the scanned values after gas has been fed in, these values having also been converted into binary signals. A digital arithmetic unit for signal processing is also provided, in the form of a microcomputer which emits values for measurement indication in an indicator device 11 or for triggering a warning signal.

Figure 2:
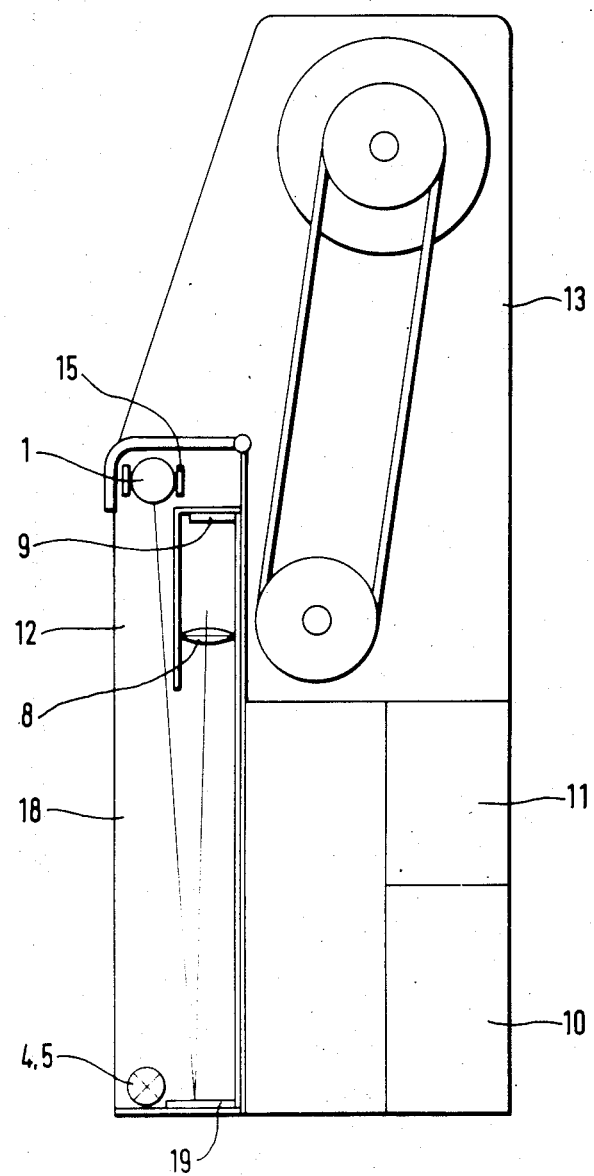
FIG. 2 is a front view of an embodiment of the apparatus of the invention incorporating the basic principle illustrated in FIG. 1; and, FIG. 3 is a partially sectional side view of the apparatus of FIG. 2.
Figure 3:
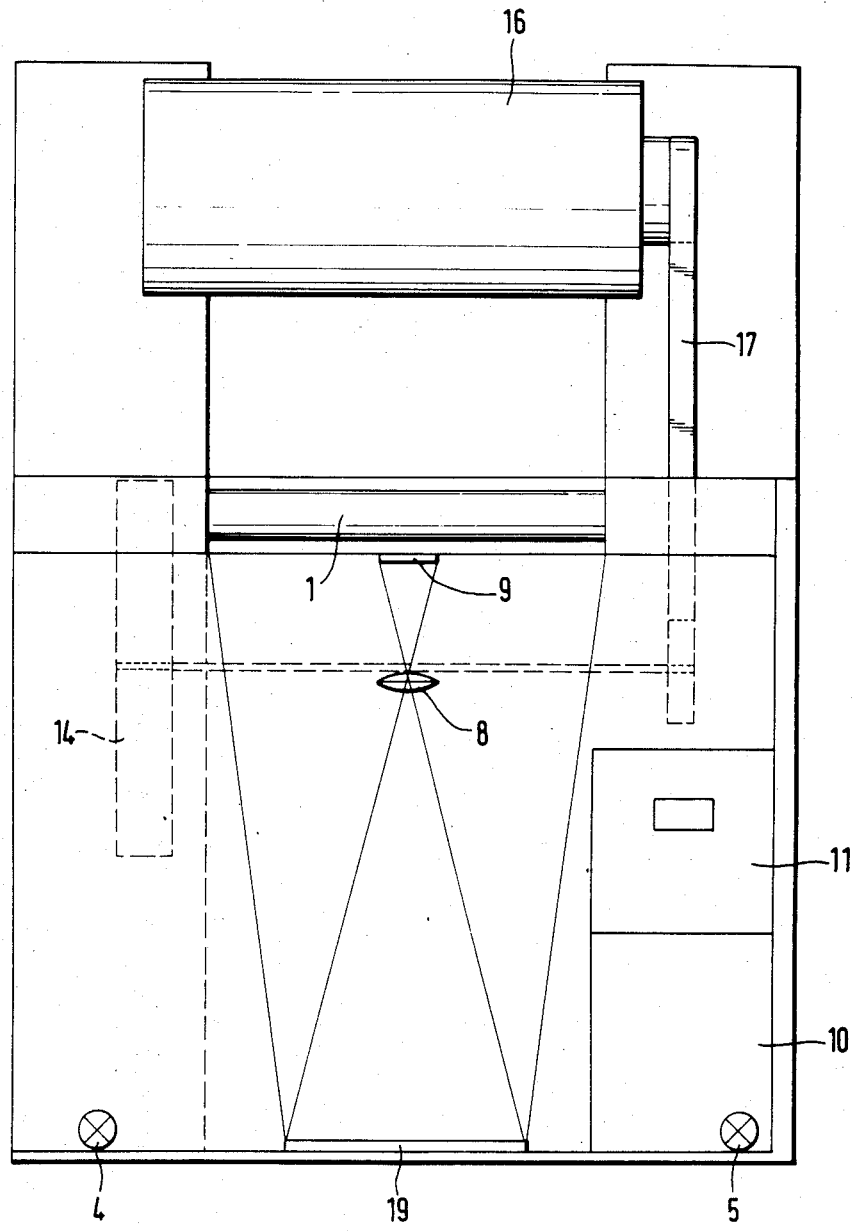

A suitable embodiment which utilizes the basic configuration illustrated in FIG. 1 is shown in FIGS. 2 and 3.

In an upper housing part 12 of a portable housing 13, there is a suction holder 15 for the testing tube, the holder 15 being connected to a flow inducer 14. A drive motor 16 is provided for driving the flow inducer 14 and is connected to the latter via a belt drive 17. By means of the flow inducer 14, ambient air is aspirated by the testing tube 1.

The two lamps 4, 5 are located in a lower housing part 18 and are symmetrically arranged with respect to a deflection mirror 19. The mirror 19 deflects the image of the illuminated testing tube 1 into the image forming lens system 8 disposed in the upper housing part 12. The diode array 9 is located behind this image forming lens system 8. The evaluation circuit 10 is in the form of an electronic circuit board and is connected directly to the indicator device 11 which produces a digital display.

When the measuring apparatus is in operation, the drive motor 16 is switched on, and as a result, ambient air is aspirated by the testing tube 1 for a defined period of time with the aid of the flow inducer 14. A migrating reaction zone 2 develops and an image thereof is formed via the image forming lens system 8 on the diode array 9. The image is enlarged as required and the length of the reaction zone determines the signal values called up by the evaluation circuit 10.

Initially, the diode array is read out without a gas charge and these values are stored in the first digital memory. In addition to a norming of the stored values, a drift correction for compensating for the influence of temperature is performed with the aid of the image of the illuminated remission surface 3 on the diode array 9. Thereafter, the location of the boundary of the reaction zone 2 is determined by reading out the diode array again, and these values are stored in the second digital memory. After this, the stored values are processed, and both the speed of migration of the reaction zone and the desired measured values (actual toxic concentration, mean value after 15 min, STEL exposition value and the like) are calculated. The measured values are emitted in the indicator device 11 or are used to trigger a warning device, not shown in the drawing.

It is further understood that the foregoing description is that of the preferred embodiments of the invention and that various changes and modifications may be made thereto without departing from the spirit and scope of the invention as defined in the appended claims.

What is claimed is:

1. A self-contained portable gas measuring and warning apparatus comprising:
    a housing;
    a testing tube mounted in a fixed position in said housing for conducting the gas therethrough the presence of which is to be detected;
    gas-flow inducing means mounted in said housing for passing the gas through said testing tube;
    light-source means for illuminating the entire length of said testing tube;
    a photoelectric scanning device for scanning said testing tube at a plurality of locations one next to the other along the direction of flow of the gas through said testing tube to detect the presence of a reaction zone migrating therethrough;
    said photoelectric scanning device including:
    optical imaging means for forming an image of said entire length of said testing tube including said reaction zone;
    a light-sensitive diode array of like sensors for receiving said image on all of said sensors and for detecting the portion of said image corresponding to said reaction zone; and,
    evaluation circuit means connected to said light-sensitive array so as to be controlled by the number of said sensors detecting said portion of said image to give a measurement signal.

2. The apparatus of claim 1, said optical imaging means being configured to generate an enlarged image of said reaction zone.

3. The apparatus of claim 1, said light-source means being disposed relative to said testing tube so as to cause said light-sensitive array to be outside of the glancing angle of said testing tube.

4. The apparatus of claim 1, said light-sensitive array being configured to deliver an analog signal corresponding to said number of said sensors covered by said image of said reaction zone.

5. The apparatus of claim 1, said testing tube having a location thereon defining the end of the evaluatable reaction zone, said apparatus further comprising reference-remission surface means provided at said end of said testing tube, said optical imaging means being configured for forming an image of said reference-remission surface means on the end of said light-sensitive array whereby said light-sensitive array provides a signal for correcting drift.

6. The apparatus of claim 1, said evaluation circuit means comprising a preamplifier connected to said light-sensitive diode array; an analog-to-digital converter connected to said preamplifier; first digital storage means for storing the scanned values before said testing tube is filled with gas; second digital storage means for storing the scanned values obtained after said testing tube has been charged with gas; a digital arithmetic unit; and, indicating means connected to said digital arithmetic unit.

7. The apparatus of claim 1, comprising:
    a housing having an upper portion and a lower portion;
    a suction holder mounted in said upper portion for holding said testing tube;
    a flow inducer mounted in said housing for inducing flow through said testing tube;

said photoelectric scanning means including a deflection mirror mounted in said lower portion of said housing for deflecting the path of the light rays from said testing tube into said optical imaging means;

said light-source means including two lamps mounted in said lower portion; and, said light-sensitive array being mounted behind and downstream of said optical imaging means.

8. A self-contained portable gas measuring and warning apparatus comprising:

a housing;

a testing tube mounted in a fixed position in said housing for conducting the gas therethrough the presence of which is to be detected;

gas-flow inducing means mounted in said housing for passing the gas through said testing tube;

light-source means for illuminating the entire length of said testing tube;

a photoelectric scanning device for scanning said testing tube at a plurality of locations one next to the other along the direction of flow of the gas through said testing tube to detect the presence of a reaction zone migrating therethrough;

said photoelectric scanning device including:

optical imaging means for forming an image of said entire length of said testing tube including said reaction zone;

a light-sensitive diode array of like sensors for receiving said image on all of said sensors and for detecting the portion of said image corresponding to said reaction zone;

evaluation circuit means connected to said light-sensitive array so as to be controlled by the number of said sensors detecting said portion of said image to give a measurement signal;

said light-sensitive diode array being mounted beneath said testing tube;

shielding means interposed between said diode array and said testing tube thereby preventing unwanted reflections from said testing tube from distorting the portion of said image corresponding to said reactive zone;

said optical imaging means being disposed directly ahead of said diode array and on the same side of said shielding means as the latter; and, deflection means mounted opposite both said testing tube and said optical imaging means for reflecting the image of said testing tube into said optical imaging means.

* * * * *